United States Patent [19]

Tan et al.

[11] Patent Number: 5,670,651

[45] Date of Patent: Sep. 23, 1997

[54] THERMOSETTING RESINS DERIVED FROM 4-HYDROXY- AND 4-TRIMETHYLSILOXY-BENZOCYCLOBUTENE

[75] Inventors: Loon-Seng Tan, Centerville; Narayanan Venkatasubramanian, Fairborn, both of Ohio

[73] Assignee: The United States of America as represented by the Secretary of the Air Force, Washington, D.C.

[21] Appl. No.: 605,343

[22] Filed: Feb. 12, 1996

[51] Int. Cl.$^6$ .................................................. C07D 263/62
[52] U.S. Cl. .......................... 548/219; 568/33; 568/312; 568/315; 568/327
[58] Field of Search .......................... 548/219; 568/33, 568/312, 315, 327

[56] References Cited

U.S. PATENT DOCUMENTS

| | | |
|---|---|---|
| 4,540,763 | 9/1985 | Kirchoff. |
| 4,642,329 | 2/1987 | Kirchoff et al.. |
| 4,724,260 | 2/1988 | Kirchoff et al.. |
| 4,743,399 | 5/1988 | Kirchoff et al.. |
| 4,812,588 | 3/1989 | Schrock. |
| 4,831,172 | 5/1989 | Hahn et al.. |
| 4,999,449 | 3/1991 | Kirchoff. |
| 5,041,550 | 8/1991 | Lea et al. .................................. 548/219 |
| 5,247,037 | 9/1993 | Kirchoff et al.. |
| 5,334,752 | 8/1994 | Martin et al. ........................ 568/327 X |
| 5,480,568 | 1/1996 | Pawloski et al. ..................... 568/33 X |

FOREIGN PATENT DOCUMENTS

D 515 170 A2  11/1992  European Pat. Off..

OTHER PUBLICATIONS

L-S Tan, N. Venkatasubramanian, M.D. Houtz and C.L. Brenner, "Thermosetting Matrix Resins Based on 4–Hydroxybenzocyclobutene", Polymer Preprints, vol. 36, No. 1, Apr. 1995, published Mar. 1, 1995, pp. 443–444.

*Primary Examiner*—Paul F. Shaver
*Attorney, Agent, or Firm*—Charles E. Bricker; Thomas L. Kundert

[57] ABSTRACT

Benzocyclobutene-terminated monomers of the formula

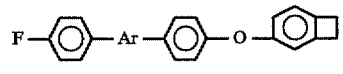

and

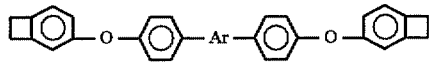

wherein Ar is —SO$_2$—, —CO—, or

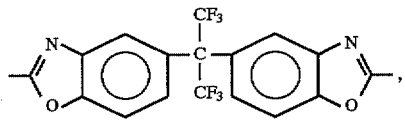

are prepared by reacting a benzocyclobutene of the formula

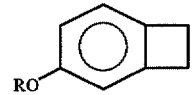

wherein R is —H or —SiMe$_3$, with a difluorophenyl compound of the formula

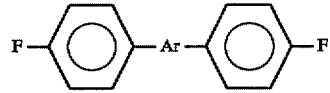

wherein Ar is as described previously, in the presence of a promoter. A mixture of the resins is obtained when potassium carbonate is employed as the promoter. The bis(benzocyclobutene)-terminated monomer is obtained when cesium fluoride is employed as the promoter.

3 Claims, No Drawings

THERMOSETTING RESINS DERIVED FROM 4-HYDROXY- AND 4-TRIMETHYLSILOXY-BENZOCYCLOBUTENE

RIGHTS OF THE GOVERNMENT

The invention described herein may be manufactured and used by or for the Government of the United States for all governmental purposes without the payment of any royalty.

BACKGROUND OF THE INVENTION

This invention relates to methods for the preparation of benzocyclobutene-terminated resins.

Benzocyclobutene (BCB)-based polymeric materials have attracted considerable attention and research interest in the area of structural and electronic applications because of the versatile chemistry of benzocyclobutene as well as the combined advantages of processability and properties. It will be understood that "benzocyclobutene" is an art-recognized term. In the commonly-used non-systematic numbering system for benzocyclobutenes, the 1- and 2-positions are in the cyclobutene ring. The 3-and 6-positions are in an aromatic ring, adjacent to the cyclobutene ring. The 4- and 5-positions are meta to the cyclobutene ring. The simplest member of the series, benzocyclobutene, is fondly identified as bicyclo[4.2.0]octa-1,3,5-triene. A compound, fondly identified as 3-bromobicyclo[4.2.0]octa-1,3,5-triene, is commonly known as 4-bromobenzocyclobutene. The common names will be used in the specification and claims.

The cure chemistry of benzocyclobutene is based upon the propensity of the four-membered ring to undergo electrocyclic ring-opening at elevated temperatures (~200° C.) to provide reactive o-quinodimethane that will undergo dimerization and polymerization, or react with an attendant dienophile to form a Diels-Alder adduct.

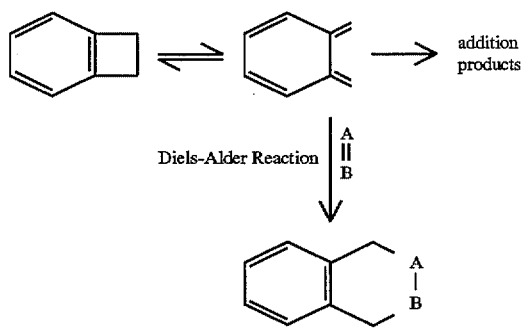

Research reports describing the synthesis and characterization of high-temperature BCB-based materials for potential structural and aerospace applications have appeared. These heat-resistant thermosets include, for example, homopolymerized bisbenzocyclobutene-terminated imide monomers and a variety of resins generated from Diels-Alder reactions of bisbenzocyclobutene-terminated imide monomers with monomers containing dienophilic end-groups such as acetylene, phenylacetylene and maleimide. Recently, the incorporation of the thermally reactive benzocyclobutene into the main chain of polymeric materials for lateral crosslinking has also been reported. The objective was to improve the compressive strength of high modulus fibers such as Kevlar® via the use of a latently crosslinkable monomer, 1,2-dihydrocyclobutabenzene 3,6-dicarboxylic acid.

4-Aminobenzocyclobutene (4-AMBCB) is a simple, polymerizable endcapping agent that has been used for the preparation of bis(benzocyclobutene) (BBCB)-terminated monomers for heat-resistant, thermosetting polyimides. Another simple BCB-endcapping agent bearing a nucleophilic center is 4-hydroxybenzocyclobutene (4-HOBCB). As its molecular structure suggests, 4-HOBCB can be used in the performance enhancement of a number of important engineering thermoplastics, such as polyethersulfones (PES), polyetherketones (PEK), polycarbonates (PC), whose syntheses require phenolic starting materials. For example, the network polymers derived from bisphenol-A polycarbonate terminated with 4-HOBCB have shown excellent solvent and ignition resistance, as well as good toughness over a broad range of crosslink densities. It has also been shown that systems derived from AB-benzocyclobutene (BCB)-maleimide (MI) monomers were easy to process and the resulting matrix materials were much tougher than other advanced thermosets for aerospace applications. 4-HOBCB was an important ingredient for a number of these AB-BCB-MI monomers. Another important advantage of 4-HOBCB over 4-AMBCB is its amenability to a large-scale, environmentally benign synthesis process using a biocatalyst in an aqueous medium.

We have prepared bis(benzocyclobutene)-terminated monomers which can be employed as matrix materials for rigid-rod polyimide-based, thermoset molecular composite systems. These monomers are also useful in preparing thermoset and thermoplastic polymeric compositions which exhibit excellent thermal stability and chemical resistance and have uses as films, coatings, adhesives, fiber-reinforced plastics, composites, structural laminates and other engineering applications.

It is therefore an object of the present invention to provide a novel method for the preparation of bis(benzocyclobutene) (BBCB)-terminated monomers.

It is a further object of the present invention to provide a new composition of matter.

Other objects and advantages of the present invention will be apparent to those skilled in the art.

SUMMARY OF THE INVENTION

In accordance with the present invention there is provided a method for making a BCB-terminated monomer of the formula

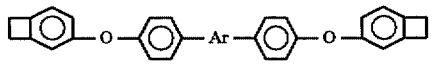

wherein Ar is —SO$_2$—, —CO—, or

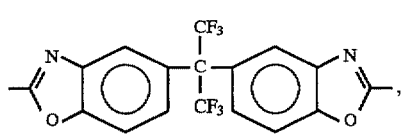

which comprises reacting a benzocyclobutene of the formula

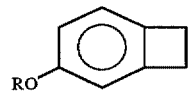

wherein R is —H or —SiMe$_3$, with a difluorophenyl compound of the formula

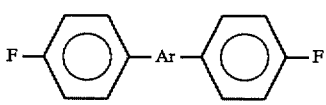

wherein Ar is as described previously, in the presence of cesium fluoride as a promoter.

There is also provided a method for making a mixture of BCB-terminated monomers of the formulas

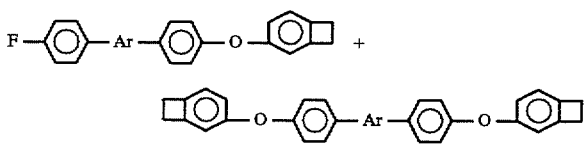

wherein Ar is —$SO_2$—, —CO—, or

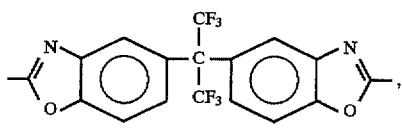

which comprises reacting a benzocyclobutene of the formula

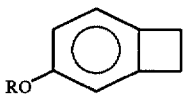

wherein R is —H or —$SiMe_3$, with a difluorophenyl compound of the formula

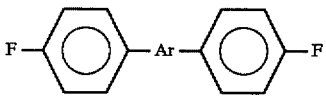

wherein Ar is as described previously, in the presence of potassium carbonate as a promoter.

DETAILED DESCRIPTION OF THE INVENTION

4-Trimethylsiloxybenzocyclobutene and 4-hydroxybenzocyclobutene can be prepared as disclosed in our co-pending application Ser. No. 08/605,242 filed Feb. 12, 1996.

p,p'-difluorobenzophenone and 4,4'-difluorophenyl sulfone are commercially available. 2,2'-Bis(2-(4-fluorophenyl)benzoxazol-6-yl) hexafluoropropane was obtained from Daychem Labs Inc., Dayton, Ohio.

The syntheses of the resins shown previously is carried out by combining the benzocyclobutene and difluoro compounds together with a reaction-promoting amount of CsF or $K_2CO_3$, in a suitable solvent and heating the mixture to about 115° to 150° C. for about 12 to 48 hours. The amounts of reactants should be at least stoichiometric; however, it is presently preferred to employ an excess of the benzocyclobutene compound, e.g., about 5 to 20% molar excess. The amount of promoter can range from about 2 to about 4 times the quantity of the difluoro compound, in molar terms.

The solvents suitable for use in the invention include the aprotic solvents dimethyl sulfoxide (DMSO), dimethylacetamide (DMAc), dimethyl formamide (DMF), N-methylpyrrolidone (NMP), and the like. The reaction should be carried out under anhydrous conditions. At the end of the reaction period, the product can be recovered and purified, as necessary, using standard procedures, such as described below in the Examples.

The resins prepared herein are useful in the preparation of polymeric compositions. In general, these polymeric compositions are prepared by heating the resin(s) to polymerization temperature. The polymerization is an addition polymerization wherein no volatiles are generated. Furthermore, no catalyst initiator or curing agents are necessary for the polymerization to take place, generally about 200° C. or greater. In certain cases, the melt polymerization of the resins allows their use in the preparation of solid parts, as coatings, in composites, as adhesives and as fibers. In one embodiment of the melt polymerization, the resin is melted at a temperature of between about 80° C. and 200° C., and thereafter poured or injected into a mold. Thereafter, pressure is applied on the melted resin in the mold. Generally, pressures of between about 100 and 2000 psi are suitable. Thereafter, the resin is heated to a temperature of between about 200° C. and 300° C. for between about 10 minutes and 3 hours. Upon cooling, the polymerized composition can be removed from the mold.

Suitable fillers and reinforcing materials are, generally, in any powder form and/or fibrous products, for example, of the type commonly used in the production of moldings based on other resins. Examples of such products include granular fillers such as quartz powder, ground shale, asbestos powder, powdered carborundum, chalk, iron powder, aluminum powder, sand, gravel and the like, as well as inorganic or organic fibers, more especially glass fibers in the usual textile forms of fibers, filaments rovings, yarns, nonwovens, mats and cloths, etc.

The following examples illustrate the invention:

EXAMPLE 1

Synthesis of p,p'-bis(4-oxybenzocyclobutenyl) benzophenone

4-Trimethylsiloxybenzocyclobutene (0.9695 g, 5 mmol) was heated with p,p'-difluorobenzophenone (0.5216 g, 2.4 mmol) in the presence of 0.923 g (6 mmol) of CsF and 10 ml anhydrous dimethylacetamide (DMAc) in the temperature range 125° C.–130° C. for 24 hrs under nitrogen. The cooled mixture was poured into 250 ml ice-cold water; the precipitated gummy, yellow solid was extracted into 300 ml $CH_2Cl_2$, the organic extract washed with 10% NaOH to remove excess 4-hydroxybenzocyclobutene and finally with water. The organic layer was dried over anhydrous $MgSO_4$ and the product, after solvent evaporation, solidified on standing (0.8 g, yield 80%). This was recrystallized from hot ethanol to an off-white crystalline solid and dried in vacuum overnight at acetone reflux (0.5 g, m.p., 102°–103° C., DSC endotherm at 106° C.).

The structure of p,p'-bis-(4)-benzocyclobutenyloxybenzophenone was confirmed by mass spec., (m/z=418, base peak). IR spectrum ($cm^{-1}$, KBr disc): 3065 (aromatic CH), 2957, 2926 ($CH_2$), 1651 (keto carbonyl), 1594 (aromatic C=C) and 1240 (aryloxy stretch). $^1$H NMR ($CDCl_3$, TMS, ppm): 3.16 (s, 8H, benzocyclobutenyl $CH_2$), 6.81–7.06 (m, 10H, aromatic) and 7.74–7.78 (d, 4H, aromatic). $^{13}$C NMR ($CDCl_3$, ppm): 29.11 (benzocyclobutenyl $CH_2$), 115.50, 116.60, 119.52, 124.12, 132.17, (protonated aromatic carbons), 131.90 (non-protonated aromatic carbon attached to carbonyl), 141.83, 147.09 (non-protonated aromatic carbons, cyclobutenyl), 154.67, 162.19 (non-protonated aromatic carbons forming ether linkage) and 194.23 (carbonyl resonance).

The DSC of the bis-BCB-terminated monomer showed a melting endotherm at 106° C. and a homopolymerization exotherm at a maximum of 262° C. The $T_g$ of the homopolymerized material, on DSC rescan, was 201° C.

A second crop of glistening white crystals (0.10 g ) was obtained from the ethanol filtrate. This was filtered and dried in vacuum overnight at 65° C., m.p. 107°–108° C. Elemental analysis: Calculated, (C, 83.23%, H, 5.29%) and found, (C, 83.42%, H, 5.03%). IR spectrum (KBr, cm$^{-1}$): 2967, 2922 ($CH_2$), 1648 (keto carbonyl), 1594 (aromatic C=C) and 1237 (aryloxy stretch).

EXAMPLE 2

Synthesis of p,p'-bis(4-oxybenzocyclobutenyl) diphenyl sulfone 1.39 gms of 4,4'-difluorophenyl sulfone (5.5 mmol) and 2.54 gms of 4-trimethylsiloxybenzocyclobutene (13.2 mmol) were heated with stirring to 130° C. in presence of 2.53 gms of CsF (16.6 mmol) and 18 ml DMAc in nitrogen for 24 hours. The dark brown solution was cooled to room temperature and poured into nearly 1 liter of ice-cold water. The off-white granular solid was isolated from the aqueous solution and was dissolved in about 500 ml $CH_2Cl_2$. The solution was washed twice with 10% NaOH to remove excess 4-hydroxybenzocyclobutene, washed with distilled water and the organic layer was kept over anhydrous $MgSO_4$. An off-white solid was obtained upon removal of $CH_2Cl_2$ followed by application of vacuum. Total weight of the crude=1.75 gms, yield 70%), m.p., 109°–111° C.

Mass spectrum showed a single component in the product with the expected structure (m/z=454, base peak). Recrystallization from ethanol resulted in a white, crystalline material and a second crop was obtained as glistening, white crystals from the ethanol filtrate. This was dried in vacuum at 65° C. overnight. The first and the second crop of crystals were used for analytical purposes. m.p., 119°–120° C., DSC endotherm at 119° C. and a homopolymerization exotherm at a peak of 262° C. Elemental analysis: Calculated: C, 73.98; H, 4.88; S, 7.05; found: C, 73.99; H, 4.95; S, 7.08. $^1$H NMR (CDCl$_3$, TMS, ppm): 3.15 (s, 8H, benzocyclobutenyl $CH_2$), 6.75–7.05 (m, 10H, aromatic protons) and 7.81–7.84 (aromatic protons, 4H). $^{13}$C NMR (CDCl$_3$, TMS, ppm): 29.08 (benzocyclobutenyl $CH_2$ ), 115.58, 117.19, 119.61, 124.22, 129.57 (protonated aromatic carbons), 135.04 (non-protonated aromatic carbons attached to sulfone), 142.36, 147.20 (non-protonated aromatic carbons, cyclobutenyl) and 153.99, 162.63 (non-protonated aromatic carbons forming ether linkage). IR spectrum (KBr, cm$^{-1}$): 2967, 2936 (benzocyclobutenyl $CH_2$ ), 1585 (aromatic C=C), 1467 ($CH_2$ deformation), 1323 (sulfone, asymmetric), 1245 (aryloxy stretch) and 1153 (sulfone, symmetric).

EXAMPLE 3

Synthesis of 2,2'-Bis(2-(4-benzocyclobutenoxy-4-phenyl) benzoxazol-6 -yl)hexafluoropropane 2,2'-Bis(2-(4-fluorophenyl)benzoxazol-6-yl) hexafluoropropane (1.50 g, 2.6 mmol), obtained from Daychem Labs Inc., Dayton, Ohio, and 4-trimethylsiloxybenzocyclobutene (1.22 g., 6.3 mmol) were heated to 140° C. in presence of 1.22 g CsF (8.0 mmol) and 18 ml DMAc under a dry nitrogen atmosphere for 24 hours. The solution obtained was deep brown in color. The solution was cooled and poured into 1 liter of ice-water with stirring and an instant off-white precipitate was formed. The precipitate was filtered off using house-vacuum and washed several times with water. When still partially dry, the solid was dissolved in methylene chloride. The pale yellow solution was stirred two times with 10% NaOH solution and shaken thoroughly in a separatory funnel. Because of the emulsion formation, more solvent was added and the layers separated after sometime. The organic layer (500 ml volume) was washed with water and dried over $MgSO_4$. Solvent removal in a rotary evaporator resulted in a viscous liquid which solidified to a glistening, foamy, off-white solid after vacuum was applied. Yield of the crude compound= 1.53 g (yield 75%).

Mass spectrum showed a single component and confirmed the presence of the expected product (m/z 774, base peak). IR spectrum (KBr, cm$^{-1}$): 2977, 2938 (benzocyclobutenyl $CH_2$ stretch), 1605 (mixed vibration, C=N and aromatic C=C), 1495 (aromatic ring), 1466 (benzocyclobutenyl $CH_2$ deformation) and 1245 (aryloxy).

The crude solid in $CH_2Cl_2$ was passed through silica gel in a filter funnel but the appearance of the recovered solid was still foamy. Attempted recrystallization from MeOH resulted in the formation of a hard, light yellow solid which was dried in vacuum at 100° C. overnight (1.1 g). HPLC using $CH_2Cl_2$ as the eluent showed a single component that eluted later than the starting benzoxazole compound. Elemental Analysis,: Calculated: C, 69.77, H, 3.64, N, 3.62; found, C, 69.58, H, 3.53, N, 3.49. IR spectrum (KBr, cm$^{-1}$): 3076 (aromatic CH), 2969, 2935 (benzocyclobutenyl $CH_2$ stretch), 1604 (aromatic C=C and C=N), 1467($CH_2$ deformation) and 1263 (aryloxy stretch). $^{13}$C NMR (CDCl$_3$, TMS): 29.09, 110.05, 115.53, 117.48, 119.50, 120.48, 122.15, 124.11, 126.93, 129.52, 130.15, 141.90, 142.19, 147.08, 150.60, 154.57, 161.94, 164.07.

About 100 mgs of a waxy white solid recrystallised from MeOH. This was dried in vacuum at 65° C. overnight. DSC analysis did not show a $T_m$, but did show a $T_g$ (when rescanned after first heating to 100° C.) at 85° C. and a BCB homopolymerization exotherm with the onset at 230° C. and a maximum at 262° C.

EXAMPLE 4

4,4'-Difluorobenzophenone (3.66 g, 16.77 mmol.), 4-hydroxybenzocyclobutene (4.38 g, 36.46 mmol.), anhydrous potassium carbonate (8.00 g, 57.88 mmol.) and 50 ml of dry N-methylpyrrolidinone were placed in a 250 ml three-necked, round-bottomed flask, which was equipped with a reflux condenser with a nitrogen adaptor, a thermometer/adaptor and a glass stopper. The initial heterogeneous mixture was heated slowly to 120° C. under nitrogen and maintained at 120°–125° C. for 17 hours. The resultant dark, heterogeneous reaction mixture was allowed to cool to room temperature and poured into a 1-liter beaker containing 30 ml of 12N HCl and about 600 ml of ice water. White precipitates appeared initially, but upon standing at room temperature for about an hour, the precipitates became brown and gummy. The product was separated by careful filtration. The filtrate was colorless and had the characteristic smell of 4-hydroxybenzocyclobutene. The gummy residue was washed with water until the pH of the washing was neutral. It was then extracted with diethyl ether. About 150 ml of the diethyl ether extract was poured into a 500 ml separatory funnel and washed with aqueous NaOH (10 g in 200 ml of water) and then with water (2×200 ml). The ether phase was then dried over anhydrous magnesium sulfate, fitered directly into a 500 ml round-bottomed flask and rotavapped, initially at room temperature and then at 70° C.

after all solvent had been removed. An amber oil was obtained and dried under vacuum overnight. Yield: 5.58 g. Mass spectrum and liquid chromatographic results of the amber oil indicated the presence of mono- (M+, 318), and di-endcapped (M+418) products. Similar results were obtained when the reaction temperature was raised to 140° C. and >10% excess of 4-hydroxybenzocyclobutene was used.

EXAMPLE 5

4,4'-Difluorophenylsulfone (3.15 g, 12.39 mmol.), 4-hydroxybenzocyclobutene (3.00 g, 24.97 mmol.), anhydrous potassium carbonate (6.90 g, 49.94 mmol.) and 60 ml of dry N-methylpyrrolidione were placed in a 250 ml three-necked, round-bottomed flask, which was equipped with a reflux condenser with a nitrogen adaptor, a thermometer/adaptor and a glass stopper. The initial heterogeneous mixture was heated slowly to 125° C. under nitrogen and maintained at 125°–130° C. for 17 hours. The resultant dark, heterogeneous reaction mixture was allowed to cool to room temperature and poured into a 1-liter beaker containing 50ml of 12N HCl and about 700 ml of ice water. White fluffy precipitates formed, but upon standing at room temperature for about 6 hours, the precipitates densified into a light brown, gummy solid. The product was separated by careful filtration. The gummy residue was washed with aqueous NaOH (5 g in 600 ml of water) and then with water until the pH of the washing was neutral. After drying overnight, the crude product was extracted with methylene chloride. About 200 ml. of the methylene chloride was dried over anhydrous magnesium sulfate, fitered directly into a 500 ml round-bottomed flask and rotavapped, initially at room temperature and then at 70° C. after all solvent had been removed. An amber oil was obtained and dried under vacuum overnight. Yield: 5.60 g. Mass spectrum and liquid chromatographic results of the amber oil indicated the presence of mono- (M+, 354), and di-endcapped (M+, 454) products. Similar results were obtained when the reaction temperature was raised to 140° C. and >10% excess of 4-hydroxybenzocyclobutene was used.

Various modifications may be made in the instant invention without departing from the spirit and scope of the appended claims.

We claim:

1. A method for making a bis(benzocyclobutene)-terminated monomer of the formula

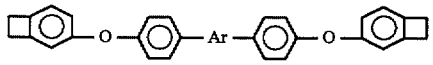

wherein Ar is —SO$_2$—, —CO—, or

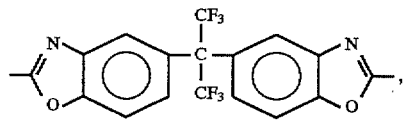

which comprises reacting a benzocyclobutene of the formula

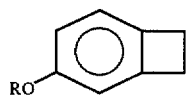

wherein R is —H or —SiMe$_3$, with a difluorophenyl compound of the formula

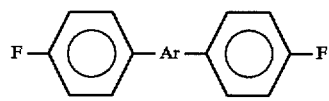

wherein Ar is as described previously, in the presence of cesium fluoride as a promoter.

2. A bis(benzocyclobutene)-terminated monomer of the formula

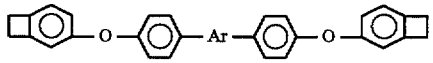

wherein Ar is

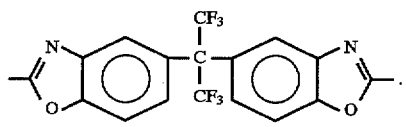

3. A method for making a mixture of benzocyclobutene-terminated monomers of the formulas

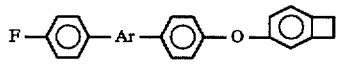

and

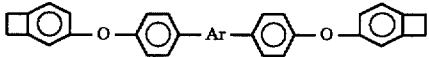

wherein Ar is —SO$_2$—, —CO—, or

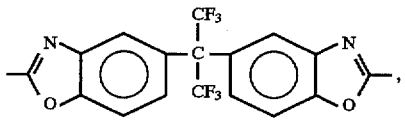

which comprises reacting a benzocyclobutene of the formula

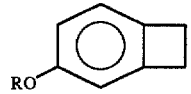

wherein R is —H or —SiMe$_3$, with a difluorophenyl compound of the formula

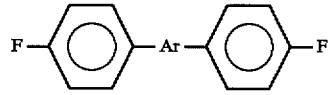

wherein Ar is as described previously, in the presence of potassium carbonate as a promoter.

* * * * *